United States Patent
Wei et al.

(10) Patent No.: US 10,457,623 B1
(45) Date of Patent: Oct. 29, 2019

(54) PROCESS FOR THE PREPARATION OF LUBIPROSTONE AND INTERMEDIATES THEREOF

(71) Applicant: CHIROGATE INTERNATIONAL INC., Yangmei (TW)

(72) Inventors: Shih-Yi Wei, Yangmei (TW); Min-Kuan Hsu, Yangmei (TW)

(73) Assignee: CHIROGATE INTERNATIONAL INC., Yangmei (TW)

( * ) Notice: Subject to any disclaimer, the term of this patent is extended or adjusted under 35 U.S.C. 154(b) by 0 days.

(21) Appl. No.: 16/034,598

(22) Filed: Jul. 13, 2018

(51) Int. Cl.
  *C07C 51/373* (2006.01)
  *C07F 7/08* (2006.01)
  *C07C 31/40* (2006.01)
  *C07D 307/06* (2006.01)

(52) U.S. Cl.
  CPC .......... *C07C 51/373* (2013.01); *C07C 31/40* (2013.01); *C07D 307/06* (2013.01); *C07F 7/0812* (2013.01); *C07C 2601/08* (2017.05)

(58) Field of Classification Search
  CPC ... C07C 51/373; C07C 31/40; C07C 2601/08; C07D 307/06; C07F 7/0812
  USPC .......................................................... 549/214
  See application file for complete search history.

(56) References Cited

U.S. PATENT DOCUMENTS

| 5,256,696 A * | 10/1993 | Ueno | A61K 31/557 514/573 |
|---|---|---|---|
| 7,253,295 B2 * | 8/2007 | Ueno | A61K 31/557 554/61 |
| 7,459,583 B2 * | 12/2008 | Ueno | A61K 31/5575 562/503 |
| 7,812,182 B2 * | 10/2010 | Hirata | C07C 405/0025 549/396 |
| 7,928,252 B2 * | 4/2011 | Alberico | C07C 405/00 549/299 |
| 8,309,744 B2 * | 11/2012 | Alberico | C07C 405/00 549/299 |
| 9,382,272 B2 * | 7/2016 | Kothakonda | C07C 69/734 |
| 9,670,234 B2 * | 6/2017 | Henschke | C07F 7/1892 |
| 2012/0065409 A1 * | 3/2012 | Kothakonda | C07C 69/734 549/214 |
| 2015/0005528 A1 * | 1/2015 | Henschke | C07C 29/143 560/121 |
| 2016/0237056 A1 * | 8/2016 | Yiannikouros | C07C 49/753 |

FOREIGN PATENT DOCUMENTS

| CN | 103787942 | * | 5/2014 |
|---|---|---|---|
| CN | 104140410 | * | 11/2014 |

OTHER PUBLICATIONS

Chemical Abstracts STN Database Record for RN 1346597-43-0, entered on Nov. 30, 2011. (Year: 2011).*
Wang; J. Med. Chem. 2000, 43, 945-952. (Year: 2000).*
Chapter 2 in: Wuts, P and Greene, T; "Greene's Protective Groups in Organic Synthesis, Fourth Edition", John Wiley & Sons, 2007, pp. 16-366. (Year: 2007).*

* cited by examiner

*Primary Examiner* — Daniel R Carcanague
(74) *Attorney, Agent, or Firm* — Ladas & Parry LLP

(57) ABSTRACT

The present invention relates to a novel process for preparing Lubiprostone and novel intermediates prepared from the process. The process of the present invention does not generate hydrogenated by-products that are difficult to be removed, and thus enables the production of Lubiprostone in an efficient and economical way.

2 Claims, No Drawings

PROCESS FOR THE PREPARATION OF LUBIPROSTONE AND INTERMEDIATES THEREOF

FIELD OF THE INVENTION

The present invention relates to a novel process of preparing Lubiprostone and novel intermediates thereof.

BACKGROUND OF THE INVENTION

Lubiprostone is an active pharmaceutical ingredient in the drug product Amitiza® for the treatment of diseases such as chronic idiopathic constipation, predominantly irritable bowel syndrome-associated constipation in women and opioid-induced constipation. Currently available methods for the synthesis of Lubiprostone disclosed in the prior art, such as in EP 0430551, U.S. Pat. Nos. 7,812,182, 7,928,252, 8,309,744, 9,382,272, and CN 103787942, use Corey lactone or derivatives thereof as a starting material to respectively construct the α-side chain and the ω-side chain of Lubiprostone by a two-step Wittig reaction as shown in the following Scheme A. However, the Corey method requires many synthetic steps and thus results in low yield.

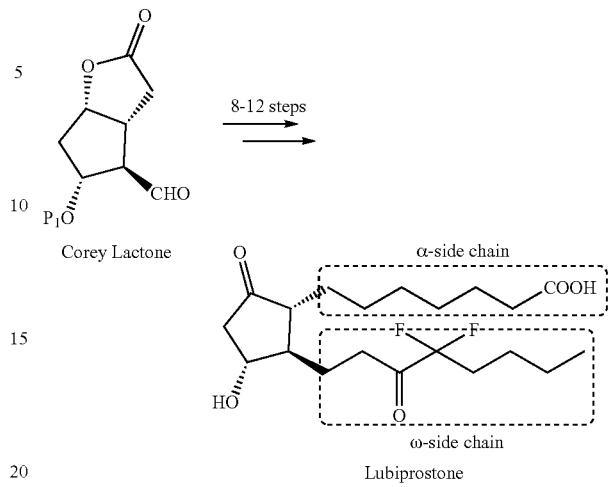

Scheme A

As shown in the following Scheme B, Lubiprostone disclosed in the prior art, such as in U.S. Pat. No. 9,670,234 and WO 2012048447, is synthesized by 1,4-conjugate addition of cyclopentenone A and a vinylboron compound or vinyl caprate B to form Lubiprostone's intermediate C with double bonds at C13-C14, C5-C6, and/or C17-C18; removing the benzyl protecting group through hydrogenation and reducing the double bonds at C13-C14, C5-C6, and/or C17-C18 to single bonds to give compound D; and carrying out three additional chemical reactions.

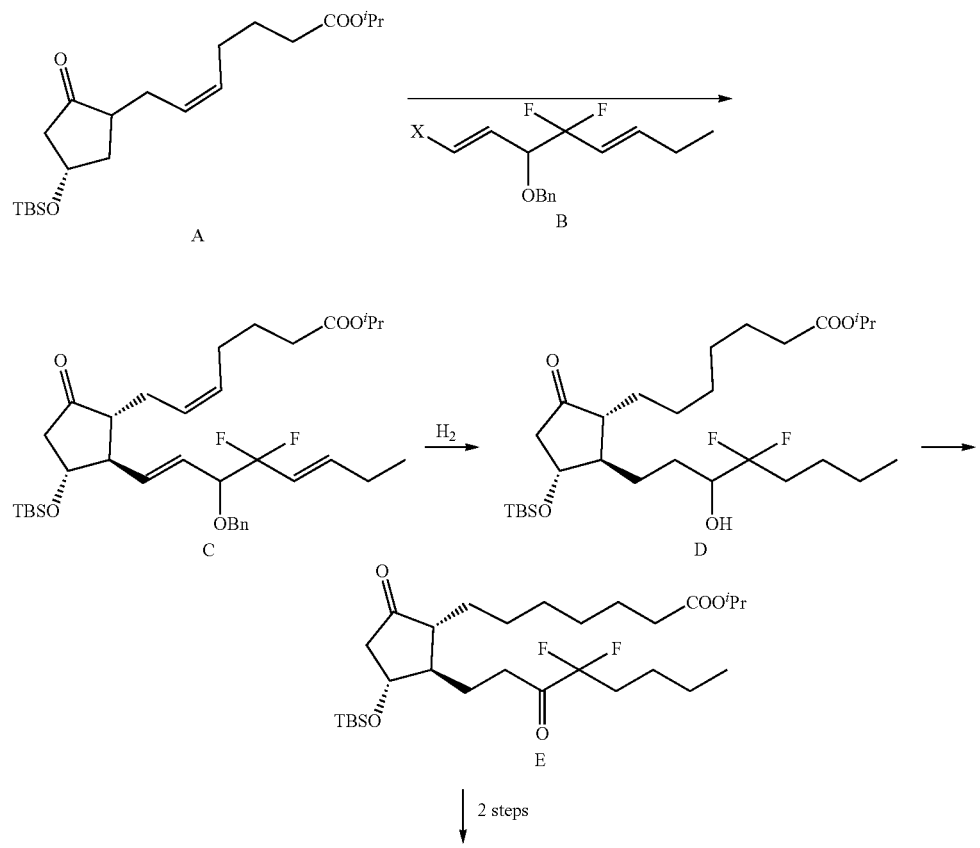

Scheme B

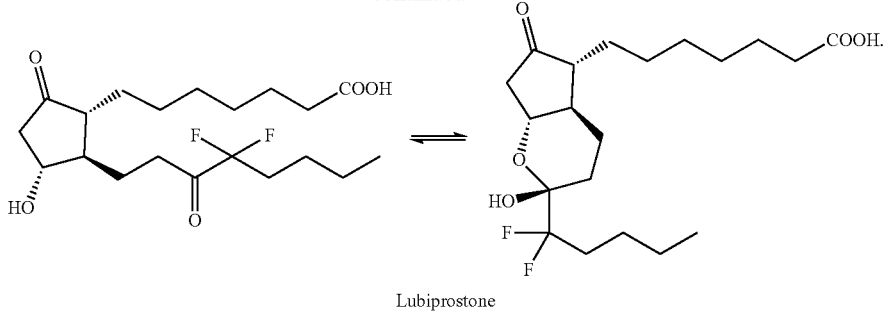

Lubiprostone

This process can more rapidly form Lubiprostone. However, due to huge steric hindrance on both sides of the double bond at C13-C14, the intermediate C is very difficult to be hydrogenated or reduced. A large amount of expensive hydrogenation catalysts must be used under high pressure and high temperatures to reduce all the double bonds to single bonds. In these circumstances, by-products are inevitably produced due to incompletely reduced double bonds, and dehydration or deoxygenation by-products or even by-products with shifted double bonds are also generated due to extreme conditions. Since these by-products are similar to the main products with single bonds in polarity, it is almost impossible to completely remove the hydrogenation by-products by using a silica gel chromatography method. Therefore, the industrial purification of Lubiprostone in mass production has encountered great difficulties.

Consequently, there is a demand for efficient and economical processes for the preparation of Lubiprostone with high yield and high purity.

SUMMARY OF THE INVENTION

In one aspect, the present invention provides a novel process for the preparation of Lubiprostone, which can efficiently solve the aforementioned conventional problems.

The process for preparing Lubiprostone comprises the steps of coupling a cyclopentenone of Formula 1:

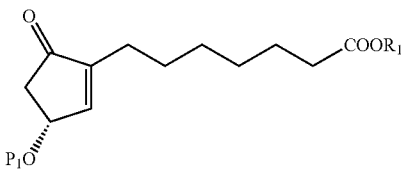

1 wherein $R_1$ is $C_{1-7}$-alkyl, aryl or aralkyl, each of which is unsubstituted or substituted by $C_{1-4}$-alkyl, nitro, halogen or alkoxy; and $P_1$ is a protective group for hydroxyl group, with a caprate derived from a compound of Formula 2a:

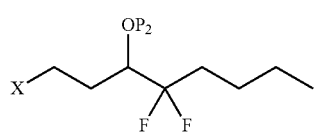

2a wherein $P_2$ is a protective group for hydroxyl group; and X is Cl, Br or I, to provide a compound of Formula 3:

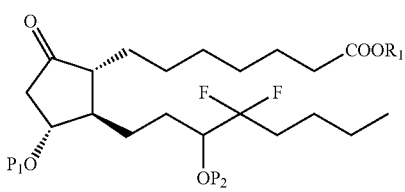

3 wherein $R_1$, $P_1$ and $P_2$ are as defined above;
removing the $P_2$ group and oxidizing the hydroxyl group in ω-side chain to form a compound of Formula 5:

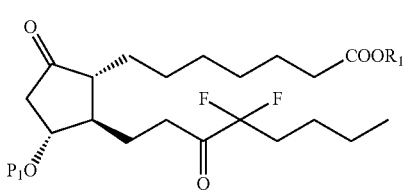

5 wherein $R_1$ and $P_1$ are as defined above; and removing the $P_1$ and $R_1$ groups.

In another aspect, the present invention provides novel intermediates useful in the production of Lubiprostone of high purity and in high yield.

DETAILED DESCRIPTION OF THE INVENTION

Herein, unless otherwise specified, the term "alkyl" refers to an aliphatic hydrocarbon group which may be straight or branched having in the chain 1 to 12 carbon atoms, preferably 1 to 8 carbon atoms, and more preferably 1 to 6 carbon atoms, such as methyl, ethyl, n-propyl, iso-propyl, t-butyl, and the like; the term "alkoxy" refers to an alkoxy group which may be straight or branched having in the chain 1 to 12 carbon atoms, preferably 1 to 8 carbon atoms, and more preferably 1 to 6 carbon atoms, such as methoxy, propoxy, tert-butoxy, pentoxy, and the like; the term "aryl" refers to a monocyclic or polycyclic aromatic hydrocarbon radical, such as phenyl, naphthyl, anthryl, phenanthryl and the like; and the term "aralkyl" refers to a straight or branched hydrocarbon containing 1 to 20 carbon atoms and one or more aryl group as described above, such as benzyl, benzhydryl, fluorenylmethyl, and the like.

When a defined radical is substituted, the substituent is selected from the group consisting of halogen, alkyl, aryl, alkoxy, aryloxy, thioalkoxy, thioaryloxy, alkylamino, arylamino, cyano, nitro, alkoxycarbonyl, arylcarbonyl, arylaminocarbonyl, alkylaminocarbonyl, and carbonyl or a heterocyclic group selected from the group consisting of pyridinyl, thiophenyl, pyranyl, furanyl, imidazolyl, morpholinyl, oxazolinyl, piperidinyl, piperazinyl, tetrahydropyranyl, pyrrolidinyl, pyrrolidinonyl, and the like, and the combinations thereof In the depiction of the compounds given throughout this description, a bold wedge (◂■) indicates a substituent in the beta-orientation (above the plane of the molecule or page), and a broken flared line (⋯⋯) indicates a substituent in the alpha-orientation (below the plane of the molecule or page).

Preparation of Lubiprostone

According to the reactions shown in the following Scheme C, there is provided a process for preparing Lubiprostone:

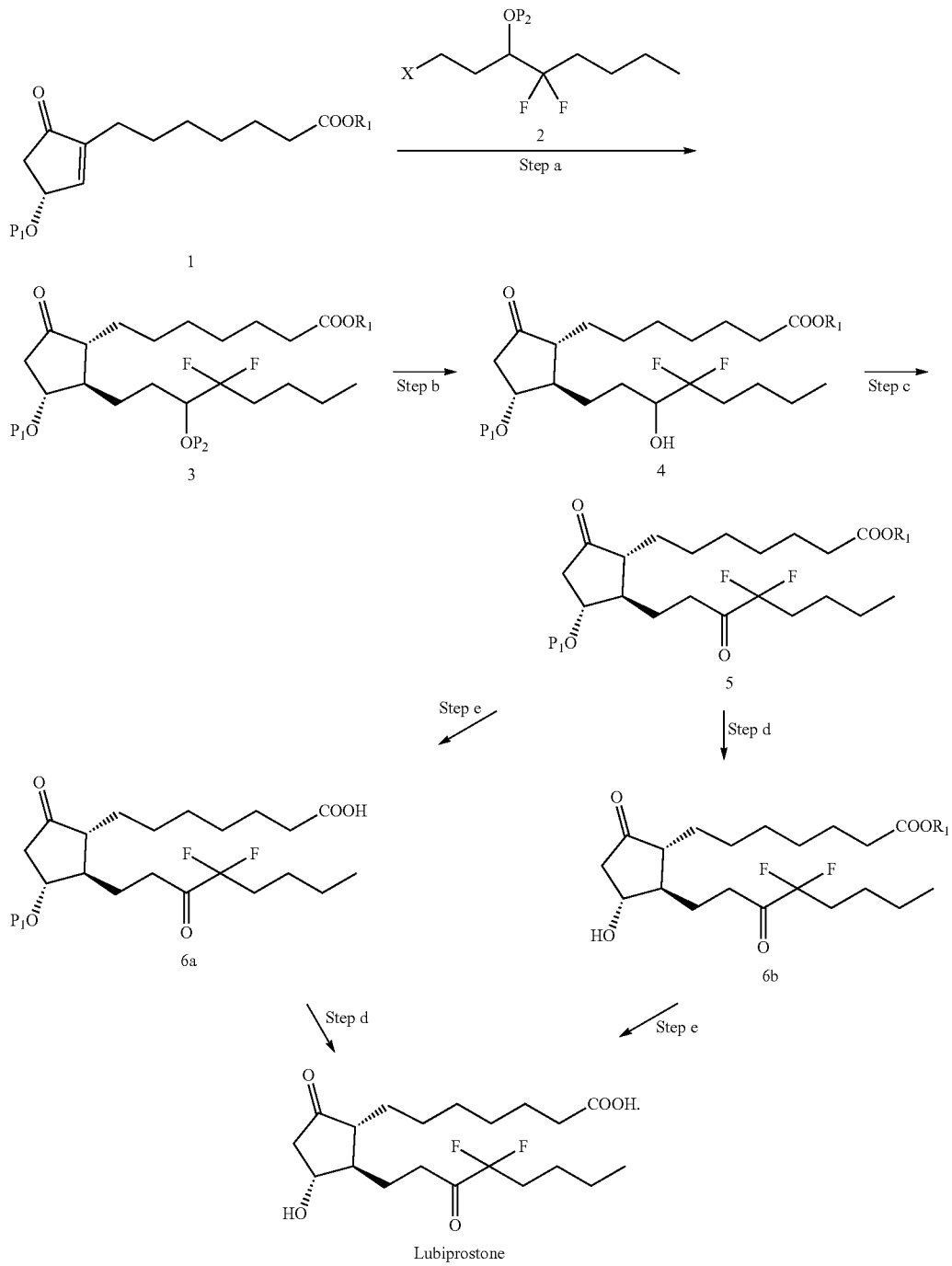

As shown in step (a) of Scheme C, the compound of Formula 3, wherein $R_1$ is $C_{1-7}$-alkyl, aryl or aralkyl, each of which is unsubstituted or substituted by $C_{1-4}$-alkyl, nitro, halogen, or alkoxy; and $P_1$ and $P_2$ are independently a protective group for hydroxyl group, is prepared by a coupling reaction, which is preferably performed at a temperature ranging from about −100° C. to about 40° C., with a ω-side chain unit of a cuprate derived from the compound of Formula 2, wherein X is Cl, Br or I; and $P_2$ is a protective group for hydroxyl group or H, of an optically active cyclopentenone of Formula 1 wherein $R_1$ is $C_{1-7}$-alkyl, aryl or aralkyl, each of which is unsubstituted or substituted by $C_{1-4}$-alkyl, nitro, halogen, or alkoxy; and $P_1$ is a protective group for hydroxyl group.

Suitable protective groups for hydroxyl groups (i.e., $P_1$ and $P_2$) include, but are not limited to, methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, allyl, benzyl, substituted benzyl, and $SiR_aR_bR_c$ wherein $R_a$, $R_b$ and $R_c$ are each independently $C_{1-8}$ alkyl, phenyl, benzyl, substituted phenyl, or substituted benzyl. Preferably, the protective groups for hydroxyl group include trimethylsilyl, triethylsilyl, tert-butyldimethylsilyl, n-octyldimethylsilyl, methoxymethyl, tetrahydrofuranyl, or tetrahydropyranyl.

Step (b) of Scheme 1 involves a deprotection reaction by selectively removing the $P_2$ protective group in the ω-side chain of the compound of Formula 3. The conditions for carrying out the deprotection reaction depend on the variable of $P_2$ and are obvious to persons skilled in the art. For example, when $P_1$ is a protective group sensitive to acid, such as tetrahydrofuranyl, and P2 is trialkylsilyl, the trialkylsilyl protective group can be selectively removed by using fluoride ions, such as tetra-butylammonium fluoride, under neutral or alkaline conditions.

Step (c) of Scheme 1 involves an oxidation reaction. The C15-OH in the compound of Formula 4 was oxidized into a keto group at proper oxidation conditions, such as Collins oxidation, Swern oxidation, PCC oxidation, PDC oxidation, and TEMPO oxidation, preferably TEMPO oxidation, to form a diketone of Formula 5 using TEMPO oxidation method.

Steps (d) and (e) of Scheme 1 respectively involve the removal of the $P_1$ protective group and the $R_1$ group, and the sequence of the two steps is interchangeable.

As shown in Step (d) of Scheme 1, the compound of Formula 5 or 6a is subjected to a deprotection reaction for removing the $P_1$ protective group. The conditions for carrying out the deprotection reaction depend on the variable of $P_1$ and are obvious to persons skilled in the art. When $P_1$ is tetrahydropyranyl, the compound of Formula 5 or 6a can be dissolved in a suitable solvent, such as methanol and a solvent mixture of acetone and water in a volumetric ratio of about 5 to about 1, treated with a deprotecting agent such as hydrogen chloride, p-toluenesulfonic acid, and pyridium p-toluenesulfonate, and stirred at room temperature for about 10 minutes to about 10 hours; and then the reaction mixture can be quenched with a base, e.g., ammonium hydroxide, and subjected to a work-up procedure conducted in a conventional manner. When $P_1$ is unsubstituted or substituted benzyl, the deprotection reaction can be achieved by using a hydrogenation catalyst in a suitable solvent and in the presence of hydrogen. Suitable hydrogenation catalyst contains a metal selected from the group consisting of palladium, platinum, rhodium, and nickel and a mixture thereof. Examples of the catalyst include Pd/C, Pt/C, and Ni. Suitable solvent can be selected from tetrahydrofuran, ethyl acetate, methanol, ethanol, toluene, and a mixture thereof.

As shown in Step (e) of Scheme 1, the compound of Formula 5 or 6b is subjected to hydrolysis reaction for removing the $R_1$ group. The conditions for carrying out the hydrolysis reaction depend on the variable of $R_1$ and are obvious to persons skilled in the art. When $R_1$ is alkyl, the compound of Formula 5 or 6b can be subjected to an enzymatic hydrolysis reaction in the presence of an enzyme, preferably a Candida antarctica lipase, such as Lipase 435, in an aqueous phase (water or a buffer), and/or an organic solvent such as hexane, toluene, tetrahydrofuran, methylisobutylketone, and a mixture thereof. When $R_1$ is unsubstituted or substituted benzyl group, the compound of Formula 5 or 6b can be subjected to a hydrogenation reaction which is conducted in the presence of a hydrogenation catalyst in a suitable solvent with hydrogen.

The novel process of the present invention requires fewer steps than the conventional synthesis methods of Lubiprostone. Suprisingly, it has also been found that the novel process produces the product with a higher yield, a higher purity and at a reduced cost. Specifically, a large amount of expensive hydrogenation catalysts has to be used in Scheme B of the aforementioned prior art process; however, in the novel process, only a small amount of the hydrogenation catalyst is used in Step (d) or (e) of Scheme C, the benzyl group can be rapidly removed. Moreover, the aforementioned by-products that are generated in the process of Scheme B are completely avoided in the novel processes, thereby effectively solving the drawbacks associated with the prior processes.

Novel Compounds of Formula 3

The present invention also pertains to a novel compound of Formula 3:

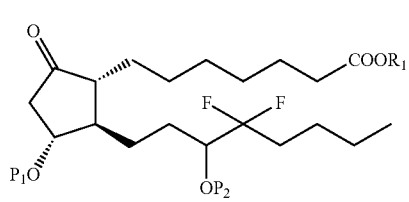

3 wherein $P_1$ and $P_2$ are independently a protecting group for hydroxyl group; and $R_1$ is $C_{1-7}$-alkyl, aryl or aralkyl, each of which is unsubstituted or substituted by $C_{1-4}$-alkyl, nitro, halogen or alkoxy.

Novel Compounds of Formula 2

The present invention further pertains to a novel compound of Formula 2:

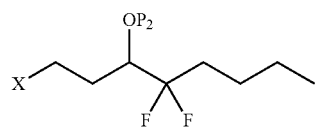

2 wherein $P_2$ is a protecting group for hydroxyl group or H; and X is Cl, Br or I.

The following examples are used to further illustrate the present invention, but are not intended to limit the scope of the present invention. Any modifications or alterations that can be easily accomplished by persons skilled in the art fall within the scope of the disclosure of the specification and the appended claims.

EXAMPLES

Example 1

Ethyl 4,4-difluoro-3-oxo-octanoate

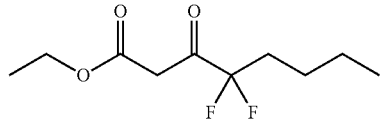

A 20-liter four-neck flask was flame dried and cooled down under nitrogen. Diisopropylamine (585 g, 5.78 mol) in 4.7 L dry tetrahydrofuran was added to the reaction flask, followed by dropwise addition of n-butyl lithium (3.6 L, 1.6 M in hexane) at −70° C. and stirred for 1 h. Then, ethyl acetate (509 g, 5.78 mol) was added to the lithium agent slowly. After 30 minutes, ethyl 2,2-difluorohexanoate (520 g, 2.89 mol) was added to the reaction flask at −70° C. The reaction mixture was stirred for 30 minutes and the reactivity was checked by using thin layer chromatography (TLC). The mixture was quenched with 5 L saturated ammonium chloride aqueous solution and stirred for 10 minutes. The mixture was phase separated and the aqueous layer was extracted with 1 L toluene. The organic layer was dried over anhydrous magnesium sulfate and the solid was filtered off. The solvent was evaporated off under vacuum to give 875 g crude ester product.

$^1$H-NMR (CDCl$_3$): δ11.957 (s, 0.5 H), 5.444 (s, 0.5 H), 4.150~4.240 (m, 2 H), 3.648 (s, 1 H), 1.953~2.034 (m, 2 H), 1.223~1.414 (m, 7 H), 0.861 (dt, 3H)

$^{13}$C-NMR (CDCl$_3$): δ 193.659 (t), 172.168, 167.352 (t), 165.754, 118.535 (t), 118.091 (t), 90.060 (t), 61.623, 60.883, 43.357, 34.048 (t), 31.938 (t), 23.805 (t), 23.046 (t), 22.279, 22.192, 13.941, 13.873, 13.607, 13.546

Example 2

4,4-Difluorooctane-1,3-diol

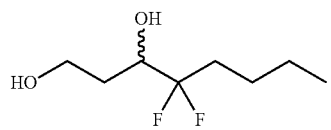

Sodium borohydride (253 g, 6.69 mol) was added to dissolve the crude ester product of Example 1 (875 g) in 4.5 L ethanol at ambient temperature. The reaction mixture was stirred for 2 h and the reactivity was checked by using TLC. Then, the reaction mixture was adjusted to a neutral solution with aqueous 3N hydrochloric acid. The aqueous solution was concentrated and ethanol was removed. The aqueous solution was extracted with 2.5 L ethyl acetate twice. The organic layer was evaporated off under vacuum. The crude 1,3-diol product was purified by chromatography on silica gel using a mixture of hexane and ethyl acetate as a gradient eluent. Yield of the 1,3-diol compound was 306 g (58%, two steps).

$^1$H-NMR (CDCl$_3$): δ 3.760~3.893(m, 5H), 1.678~1.922 (m, 4H), 1.291~1.505 (br s, 4H), 0.897 (t, 3H)

$^{13}$C-NMR (CDCl$_3$): δ 123.997 (t), 71.396 (t), 60.040, 32.040 (t), 31.561, 23.379 (t), 22.461, 13.777

Example 3

4,4-difluoro-1-iodooctan-3-ol

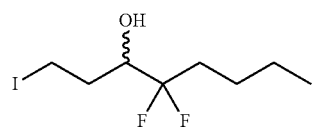

A 12-liter four-neck flask was flame dried and cooled down under nitrogen. 4,4-difluorooctane-1,3-diol of Example 2 (607 g, 3.33 mol) in 6 L dry THF was added to the reaction flask. Imidazole (803 g, 11.8 mol) and triphenyl phosphine (2.2 kg, 8.4 mol) were also added into this flask. In the homogenous mixture, iodine (2.56 kg, 10.1 mol) was added to the reaction flask at 0° C. and continuously stirred for 3 h. Then, the reaction mixture was quenched with 20% aqueous Na$_2$S$_2$O$_3$, and 3 L ethyl acetate was added and stirred for 30 minutes. The reaction mixture was phase separated. The organic layer was dried over anhydrous MgSO$_4$, the solid was filtered off, and the solvent was evaporated under vacuum. The crude iodo product was purified by chromatography on silica gel using a mixture of hexane and ethyl acetate as a gradient eluent. Yield of the iodo compound was 737 g (75%), $^1$H-NMR (CDCl$_3$): δ 3.858 (q, 1H), 3.363~3.406 (m, 1H), 3.267~3.319 (m, 1 H), 2.211 (br s, 1H), 2.083~2.151 (m, 1H), 1.761~2.013 (m, 3H), 1.462~1.527 (m, 2H), 1.328~1.402 (m, 2H), 0.924 (t, 3H)

$^{13}$C-NMR (CDCl$_3$): δ 123.786 (t), 72.748 (t), 33.634, 32.168 (dd), 23.336 (t), 22.481, 13.786, 1.893

Example 4

(4,4-difluoro-1-iodooctan-3-yloxy)-trimethylsilane

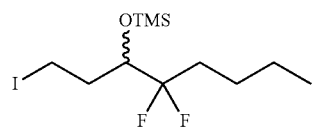

4,4-difluoro-1-iodooctan-3-ol of Example 3 (737 g, 2.5 mol) of Example 3 in 7.4 L ethyl acetate was added to a 12-liter four-neck flask, followed by addition of imidazole (2.58 kg, 3.79 mol). In the homogenous mixture, chlorotrimethylsilane (326 g, 3 mol) was added to this flask. The white solid was filtered off from the reaction mixture, and the filtrate was extracted with 3.5 L saturated aqueous NaHCO$_3$ twice. The organic layer was dried over anhydrous MgSO$_4$, the solid was filtered off, and the solvent was evaporated under vacuum. The crude silane product was purified by chromatography on silica gel using a mixture of hexane and ethyl acetate as a gradient eluent. Yield of the silane compound was 780 g (85%).

$^1$H-NMR (CDCl$_3$): δ 3.846~3.908 (m, 1H), 3.290~3.331 (m, 1H), 3.117~3.168 (m, 1H), 1.635~2.060 (m, 4H), 1.312~1.507 (m, 4H), 0.914 (t, 3H), 0.173 (br s, 9H)

$^{13}$C-NMR (CDCl$_3$): δ 123.817 (t), 73.977 (dd), 34.967 (dd), 32.450 (t), 23.115 (t), 22.542, 13.794, 2.313, 0.222

Example 5

(4,4-difluoro-1-iodooctan-3-yloxy)-triethylsilane

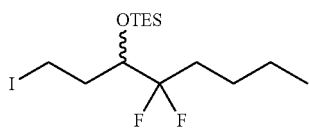

4,4-difluoro-1-iodooctan-3-ol of Example 3 (174 g, 0.60 mol) in 1.8 L ethyl acetate was added to a 5-liter four-neck flask, followed by addition of imidazole (61.3 g, 0.90 mol). In the homogenous mixture, chlorotriethylsilane (109 g, 0.72 mol) was added to this flask. Then, the white solid was filtered off from the reaction mixture and the filtrate was extracted with 1.5 L saturated aqueous NaHCO$_3$ twice. The organic layer was dried over anhydrous MgSO$_4$, the solid was filtered off, and the solvent was evaporated under vacuum. The crude silane product was purified by chromatography on silica gel using a mixture of hexane and ethyl acetate as a gradient eluent. Yield of the silane compound was 182 g (75%).

$^1$H-NMR (CDCl$_3$): δ 3.850~3.890 (m, 1H), 3.318 (br s, 1H), 3.157~3.217 (m, 1H), 1.261~2.084 (m, 8H), 0.908~0.996 (m, 12H), 0.647~0.704 (m, 6H)

$^{13}$C-NMR (CDCl$_3$): δ 124.000 (t), 74.035 (dd), 36.000 (d), 31.292 (t), 23.087 (t), 22.590, 13.831, 6.795, 5.000, 1.986

Example 6

Benzyl 7-(3R-hydroxy-5-oxo-cyclopent-1-enyl)-heptanoate

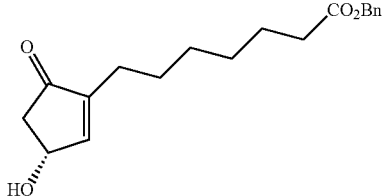 [SMILES: O=C(CCCCCCC1=C[C@H](O)CC1=O)OCc1ccccc1]

7-(3R-hydroxy-5-oxo-cyclopent-1-enyl)heptanoic acid (50 g, 0.22 mol) in 500 ml N,N-dimethyl formamide (DMF) was added to 1-liter tree-neck round bottom flask, followed by addition of potassium carbonate (91.2 g, 0.66 mol) and benzyl chloride (55.7 g, 0.44 mol). The reaction mixture was heated at 50 to 60° C. for 1 h. After cooling down the mixture at room temperature, the solid was filtered off and the filtrate was sequentially extracted with 500 ml water twice. The organic layer was dried over anhydrous MgSO$_4$, the solid was filtered off, and the solvent was evaporated under vacuum. The crude ester product was purified by chromatography on silica gel using a mixture of hexane and ethyl acetate as a gradient eluent. Yield of the benzyl compound was 56 g (80%).

$^1$H-NMR (CDCl$_3$): δ 7.313~7.360 (m, 5H), 7.125~7.131 (m, 1H), 5.103 (s, 2H), 4.930 (br s, 1H), 2.797(dd, 1 H), 2.143~2.362 (m, 5H), 1.300~1.649 (m, 9H)

$^{13}$C-NMR (CDCl$_3$): δ 206.267, 173.674, 155.841, 147.96, 136.023, 128.554, 128.201, 128.182, 68.519, 66.147, 44.871, 34.215, 28.848, 28.731, 27.141, 24.757, 24.325

Example 7

4-methoxybenzyl 7-(3R-hydroxy-5-oxo-cyclopent-1-enyl)-heptanoate

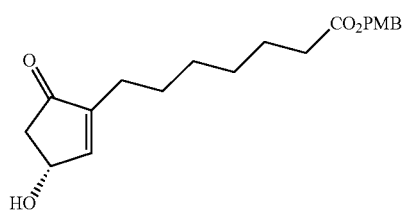

7-(3R-hydroxy-5-oxo-cyclopent-1-enyl)heptanoic acid (50 g, 0.22 mol) in 500 ml DMF was added to 1-liter tree-neck round bottom flask, followed by addition of potassium carbonate (91.2 g, 0.66 mol) and 4-methoxybenzyl chloride (68.9 g, 0.44 mol). The reaction mixture was heated at 50 to 60° C. for 1 h. After cooling down the mixture at room temperature, the solid was filtered off and the filtrate was sequentially extracted with 500 ml water twice. The organic layer was dried over anhydrous MgSO$_4$, the solid was filtered off, and the solvent was evaporated under vacuum. The crude ester product was purified by chromatography on silica gel using a mixture of hexane and ethyl acetate as a gradient eluent. Yield of the ester compound was 57 g (74%).

$^1$H-NMR (CDCl$_3$): δ 7.285 (d, 2H), 7.148~7.1510 (m, 1H), 6.884 (d, 2 H), 5.034 (s, 2H), 4.912~4.922 (m, 1H), 3.797 (s, 3H), 2.782 (dd, 1H), 2.279~2.328 (m, 3H), 2.147 (t, 2H), 1.295~1.622(m, 9H)

$^{13}$C-NMR (CDCl$_3$): δ 206.663, 173.736, 159.363, 156.354, 147.451, 129.896, 127.919, 113.749, 68.131, 65.835, 55.115, 44.674, 34.084, 28.684, 28.546, 26.971, 24.583, 24.135

Example 8

Benzyl 7-[5-oxo-3R-(tetrahydrofuranyl-2-yloxy)-cyclopent-1-enyl]heptanoate

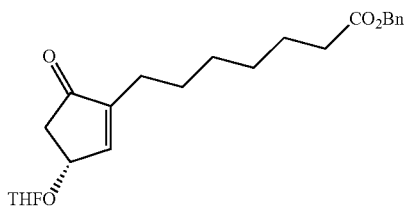

Benzyl 7-(3R-hydroxy-5-oxo-cyclopent-1-enyl)-heptanoate of Example 6 (56 g, 0.18 mol) in 500 ml dichloromethane (DCM) was added to 1-liter tree-neck round bottom flask, followed by addition of 2,3-dihydrofuran (15 g, 0.22 mol) and a catalytic amount of p-toluenesulfonic acid monohydrate. The reaction mixture was stirred for 1 h. The reaction mixture was quenched with saturated aqueous NaHCO$_3$ and then was phase separated. The organic layer was dried over anhydrous MgSO$_4$, the solid was filtered off, and the solvent was evaporated under vacuum. The crude product was purified by chromatography on silica gel using a mixture of hexane and ethyl acetate as a gradient eluent. Yield of the title compound was 63 g (92%).

$^1$H-NMR (CDCl$_3$): δ 7.308~7.377 (m, 5H), 7.198~7.202 (m, 0.5H), 7.152~7.156 (m, 0.5H), 5.333~5.341 (m, 0.5H), 5.269~5.275 (m, 0.5H), 5.110 (s, 2H), 4.817~4.827 (m, 0.5H), 4.733~4.743 (m, 0.5H), 3.878~3.947 (m, 2H), 2.764 (ddd, 1H), 2.289~2.391 (m, 3H), 2.146~2.173 (m, 2H), 1.625~1.991 (m, 4H), 1.312~1.488 (m, 8H)

$^{13}$C-NMR (CDCl$_3$): δ 206.548 (205.923), 173.482, 155.695 (153.694), 148.267 (147.715), 135.967, 128.447, 128.095, 128.083, 104.052 (103.546), 73.274 (72.722), 67.169 (67.008), 65.996, 43.762 (42.106), 34.134, 32.532 (32.440), 28.875 (28.860), 28.707 (28.699), 27.066 (27.036), 24.701 (24.682), 24.357 (24.341), 23.299

Example 9

4-Methoxybenzyl 7-[5-oxo-3R-(tetrahydrofuranyl-2-yloxy)-cyclopent-1-enyl]-heptanoate

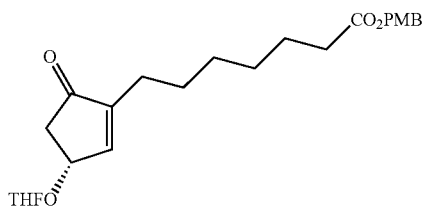

4methoxybenzyl 7-(3R-hydroxy-5-oxo-cyclopent-1-enyl)-heptanoate of Example 7 (150 g, 0.43 mol) in 1.5 L DCM was added to 3-liter tree-neck round bottom flask, followed by addition of 2,3-dihydrofuran (45 g, 0.65 mol) and a catalytic amount of p-toluenesulfonic acid monohydrate. The reaction mixture was stirred for 1 h. The reaction mixture was quenched with 100 ml saturated aqueous NaHCO$_3$ and then was phase separated. The organic layer was dried over anhydrous MgSO$_4$, the solid was filtered off, and the solvent was evaporated under vacuum. The crude product was purified by chromatography on silica gel using a mixture of hexane and ethyl acetate as a gradient eluent. Yield of the title compound was 170 g (94%).

$^1$H-NMR (CDCl$_3$): δ 7.245~7.275 (m, 2H), 7.173~7.177 (m, 0.5H), 7.127~7.131 (m, 0.5H), 6.838~6.862 (m, 2H), 5.301~5.309 (m, 0.5H), 5.235~5.243 (m, 0.5H), 5.010 (s, 2 H), 4.781~4.792 (m, 0.5H), 4.699~4.708 (m, 0.5H), 3.845~3.916 (m, 2H) 3.767 (s, 3H), 2.727 (dd, 1H), 2.254~2.357 (m, 3H), 2.125 (t, 2H), 1.805~2.009 (m, 4H), 1.590 (t, 2H), 1.445 (t, 2H), 1.272~1.296 (m, 4H)

$^{13}$C-NMR (CDCl$_3$): δ 206.449 (205.835), 173.448, 159.344, 155.637 (153.652), 148.106 (147.562), 129.854, 128.329, 127.972, 113.684 (113.607), 103.922 (103.427), 73.163 (72.623), 67.039 (66.878), 65.693, 55.038, 43.636 (41.976), 34.046, 32.410 (32.321), 28.753 (28.738), 28.573 (28.561), 26.952 (26.921), 24.587 (24.568), 24.230 (24.219), 23.192 (23.184)

Example 10

Benzyl 7-(3R-benzyloxy-5-oxo-cyclopent-1-enyl)-heptanoate

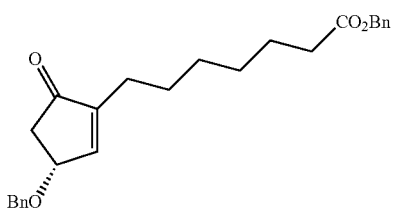 [SMILES: O=C(CCCCCCC1=C[C@H](OCc2ccccc2)CC1=O)OCc1ccccc1]

Benzyl 7-(3R-hydroxy-5-oxo-cyclopent-1-enyl)-heptanoate (50 g, 0.16 mol) in 500 ml DMF was added to 1-liter tree-neck round bottom flask at 0° C. and sodium hydride (7.1 g, 0.18 mol) was added to this flask while stirring for 30 minutes. Then, benzyl bromide (41 g, 0.24 mol) was added and the reaction mixture was warmed up to room temperature. The reaction mixture was stirred for 1 h and cooled down to −10° C. 250 ml saturated aqueous NaCl was added to the mixture, and the mixture was extracted with 500 ml ethyl acetate. The organic layer was dried over anhydrous MgSO$_4$, the solid was filtered off, and the solvent was evaporated under vacuum. The crude product was purified by chromatography on silica gel using a mixture of hexane and ethyl acetate as a gradient eluent. Yield of the title compound was 45 g (70%).

$^1$H-NMR (CDCl$_3$): δ 7.296~7.370 (m, 10H), 7.186~7.198 (m, 1H), 5.114 (s, 2H), 4.571~4.679 (m, 3H), 2.711 (dd, 1H), 2.330~2.418 (m, 3H), 2.171 (t, 2H), 1.68~1.60 (m, 2H), 1.49~1.44 (m, 2H), 1.261~1.676 (m, 8H)

$^{13}$C-NMR (CDCl$_3$): δ 205.709, 173.541, 153.803, 148.490, 137.677, 136.102, 128.565, 128,543, 128.178, 127, 992, 127.882, 74.974, 71.722, 66.086, 42.219, 34.237, 28.947, 28.791, 27.171, 24.788, 24.469

Example 11

Benzyl 7-[(1R,2R,3R)-2-(4,4-difluoro-3-trimethylsilyloctyl)-5-oxo-3-(tetrahydrofuranyl-2-yloxy) cyclopentyl]heptanoate

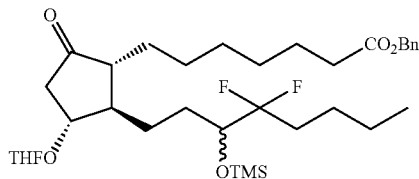

A 3-liter three-necked flask was flame dried and then cooled down under nitrogen. (4,4-difluoro-1-iodooctan-3-yloxy)-trimethylsilane of Example 4 (56.6 g, 0.16 mol) and 570 ml ether were added to the reaction flask, followed by dropwise addition of tert-butyl-lithium (190 ml, 16% in pentane) at −70° C. A suspension solution of copper cyanide (7.2 g, 0.08 mol) in 280 ml ether was cooled down to −70° C. and added to the reaction flask while stirring for 30 minutes. Then, a solution of benzyl 7-[5-oxo-3R-(tetrahydrofuranyl-2-yloxy)-cyclopent-1-enyl]heptanoate of Example 8 (19.3 g, 0.05 mol) in 200 ml ether at −70° C. was added to the reaction mixture and the mixture was warmed up to 0° C. The reaction mixture was quenched with 450 ml saturated aqueous ammonium chloride containing 50 ml ammonium hydroxide. The reaction mixture was phase separated and the aqueous layer was extracted with ethyl acetate. The organic layers were combined and dried over anhydrous MgSO$_4$. The solid was filtered off and the organic solvent was evaporated off under vacuum. The crude product was purified by chromatography on silica gel using a mixture of hexane and ethyl acetate as a gradient eluent. Yield of the title compound was 29 g (92%).

$^1$H-NMR (CDCl$_3$): δ 7.271~7.308 (m, 5H), 5.171 (br s, 1H), 5.071 (s, 2H), 3.664~4.078 (m, 4H) 2.700~2.713 (m, 1H) 1.200~2.317 (m, 29H), 0.895 (t, 3 H), 0.113 (s, 9H)

$^{13}$C-NMR (CDCl$_3$): δ 216.527 (215.661), 172.903, 135.886, 128.115, 127.810, 127.774, 124.999 (t), 104.191, 101.403 (101.345), 78.213, 74.517 (74.170), 66.713 (66, 663), 66. 549 (66.465), 53.274 (53.134), 52.960 (52.705), 46.130 (46.097), 45.915 (45.882), 43.531 (43.498), 33.780, 32.179, 30.760 (t), 29.061, 28.591, 26.248, 24.499, 23.030, 22.841, 22.280, 13.519, −0.052

Example 12

4-Methoxybenzyl 7-[(1R,2R,3R)-2-(4,4-difluoro-3-trimethylsilyloctyl)-5-oxo-3-(tetrahydrofuranyl-2-yloxy) cyclopentyl]heptanoate

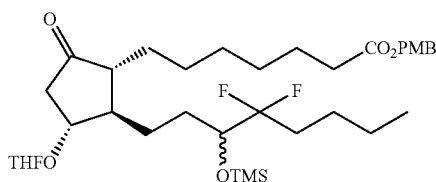

A 12-liter four-necked flask was flame dried and then cooled down under nitrogen. (4,4-difluoro-1-iodooctan-3-yloxy)-trimethylsilane of Example 4 (393.4 g, 1.08 mol) and 4 L ether were added to the reaction flask, followed by dropwise addition of turt-butyl-lithium (1.3 L, 16% in pentane) at −70° C. A suspension solution of copper cyanide (48.4 g, 0.54 mol) in 1 L ether was cooled down to −70° C. and added to the reaction flask while stirring for 30 minutes. Then, a solution of 4-methoxybenzyl 7-[5-oxo-3R-(tetrahydrofuranyl-2-yloxy)-cyclopent-1-enyl]heptanoate of Example 9 (150 g, 0.36 mol) in 1.5 L ether at −70° C. was added to the reaction mixture and the mixture was warmed up to 0° C. The reaction mixture was quenched with 2.7 L saturated aqueous ammonium chloride containing 300 ml ammonium hydroxide. The reaction mixture was phase separated and the aqueous layer was extracted with ethyl acetate. The organic layers were combined and dried over anhydrous MgSO$_4$. The solid was filtered off and the organic solvent was evaporated off under vacuum. The crude product was purified by chromatography on silica gel using a mixture of hexane and ethyl acetate as a gradient eluent. Yield of the title compound was 190 g (80%).

$^1$H-NMR (CDCl$_3$): δ 7.259~7.291 (m, 2H), 6.867~6.890 (m, 2H), 5.100~5.200 (m, 1H), 5.031 (s, 2H), 3.617~3.927 (m, 7H), 0.851~2.788 (m, 33H), 0.009 (s, 9H)

$^{13}$C-NMR (CDCl$_3$): δ 217.510 (216.607), 173.668, 159.557, 130.031, 128.217, 124.369, 121.917, 113.909, 104.634 (104.558), 84.762, 74.978 (74. 606), 72.534, 66.940 (66.885), 53.778 (53.596), 52.442 (52.156), 46.997 (46.431), 44.700 (43.926), 34.279, 32.389, 31.129 (t), 29.459, 29.262, 28.707 (28.472), 27.559, 26.863 (26.620), 24.874, 23.364, 23.144, 22.635, 13.884, 0.547

Example 13

Benzyl 7-[(1R, 2R, 3R)-3-benzyloxy-2-(4,4-ditfluoro-3-trimethylsilylostyl)]-5-oxo-cyclopenty-1-heptanoate

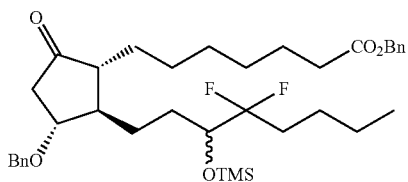

A 1-liter three-necked flask was flame dried and then cooled down under nitrogen. (4,4-difluoro-1-iodooctan-3-yloxy)-trimethylsilane of Example 4 (27.3 g, 75 mmol) and 270 ml ether were added to the reaction flask, followed by dropwise addition of tert-butyl-lithium (90 ml, 16% in pentane) at −70° C. A suspension solution of copper cyanide (3.36 g, 38 mmol) in 70 ml ether was cooled down to −70° C. and added to the reaction flask while stirring for 30 minutes. Then, a solution of benzyl 7-[5-oxo-3R-(tetrahydrofuranyl-2-yloxy)-cyclopent-1-enyl]heptanoate of Example 8 (10 g, 25 mmol) in 100 ml ether at −70° C. was added to the reaction mixture and the mixture was warmed up to 0° C. The reaction mixture was quenched with 270 ml saturated aqueous ammonium chloride containing 30 ml ammonium hydroxide. The reaction mixture was phase separated and the aqueous layer was extracted with ethyl acetate. The organic layers were combined and dried over anhydrous MgSO$_4$. The solid was filtered off and the organic solvent was evaporated off under vacuum. The crude product was purified by chromatography on silica gel using a mixture of hexane and ethyl acetate as a gradient eluent. Yield of the title compound was 13 g (81%)

$^1$H-NMR (CDCl$_3$): δ 7.325~7.364 (m, 10H), 5.118 (s, 2H), 4.453~4.584 (m, 2H), 3.304~4.043 (m, 2H), 0.911~2.70 (m, 29H), 0.113~0.145 (m, 9H)

$^{13}$C-NMR (CDCl$_3$): δ 217.474 (216.749), 173.541, 137.860 (t), 136.133, 128.531, 128.478, 128. 387, 128.163, 127.822, 127.772, 127.715, 79.308 (79.103), 71.631 (70.936), 70.887(70.386), 66.052, 53.744 (53.684), 50.519 (50.473), 46.553 (46.443), 44.222 (43.976), 34.268 33.399, 32.526, 29.414, 28.928, 27.805, 27.710, 27.577 (20.501), 24.905 (24.882), 22.628, 113.519, 0.328

Example 14

Benzyl 7-[(1R, 2R, 3R)-2-(4,4-difluoro-3-triethylsilyloctyl)-5-oxo-3-(tetrahydrofuranyl-2-yloxy) cyclopentyl]heptanoate

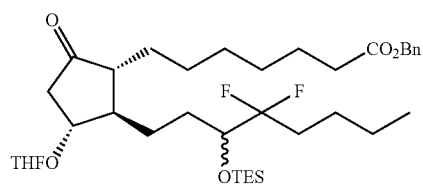

A 1-liter three-necked flask was flame dried and then cooled down under nitrogen. (4,4-difluoro-1-iodooctan-3-yloxy)-triethylsilane of Example 5 (36.5 g, 0.09 mol) and 360 ml ether were added to the reaction flask, followed by dropwise addition of tert-butyl-lithium (110 ml, 16% in pentane) at −70° C. A suspension solution of copper cyanide (4.5 g, 0.05 mol) in 90 ml ether was cooled down to −70° C. and added to the reaction flask while stirring for 30 minutes. Then, a solution of benzyl 7-[5-oxo-3R-(tetrahydrofuranyl-2-yloxy)-cyclopent-1-enyl]heptanoate of Example 8 (11.6 g, 0.03 mol) in 120 ml ether at −70° C. was added to the reaction mixture and the mixture was warmed up to 0° C. The reaction mixture was quenched with 270 ml saturated aqueous ammonium chloride containing 30 ml ammonium hydroxide. The reaction mixture was phase separated and the aqueous layer was extracted with ethyl acetate. The organic layers were combined and dried over anhydrous MgSO$_4$. The solid was filtered off and the organic solvent was evaporated off under vacuum. The crude product was purified by chromatography on silica gel using a mixture of hexane and ethyl acetate as a gradient eluent. Yield of the title compound was 16.6 g (87%).

$^1$H-NMR (CDCl$_3$): δ 7.250~7.378 (m, 5H), 5.192~5.202 (m, 0.5H), 5.110 (s, 2H), 4.078~4.120 (m, 0.5H), 3.720~3.912 (m, 4H), 2.692~2.787 (m, 1H), 2.333 (t, 2H), 1.195~2.267 (m, 27H), 0.901~0.974 (m, 12H), 0.572~0.676 (m, 6H)

$^{13}$C-NMR (CDCl$_3$): δ 217.495 (216.599), 173.569, 136.081, 128.521, 128.376, 128.156, 124.475 (t), 104.649 (101.757), 78.553, 74.054 (74.530), 67.715 (66, 925), 66.060 (t), 53.862 (53.505), 53.399 (53.148), 46.454 (t), 43,972 (43.926), 34,233, 32.503. 30.863 (30.628), 29.391, 28.958, 28.578, 28.427 (28.328), 26.613, 24.882, 23.349, 23.083 (23.045), 22.650, 13.891, 6.840, 4.957

Example 15

4-Methoxybenzyl 7-[(1R,2R,3R)-2-(4,4-difluoro-3-triethylsilyloctyl)-5-oxo-3-(tetrahydrofuranyl-2-yloxy)cyclopentyl]heptanoate

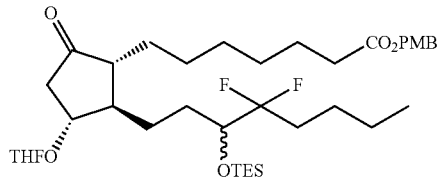

A 1-liter tree-necked flask was flame dried and then cooled down under nitrogen. (4,4-difluoro-1-iodooctan-3-yloxy)-triethylsilane of Example 5 (36.5 g, 0.09 mol) and 360 ml ether were added to the reaction flask, followed by dropwise addition of tert-butyl-lithium (110 ml, 16% in pentane) at −70° C. A suspension solution of copper cyanide (4.5 g, 0.05 mol) in 1 L ether was cooled down to −70° C. and added to the reaction flask while stirring for 30 minutes. Then, a solution of 4-methoxybenzyl 7-[5-oxo-3R-(tetrahydrofuranyl-2-yloxy)-cyclopent-1-enyl] heptanoate of Example 9 (12.5 g, 0.03 mol) in 125 ml ether at −70° C. was added to the reaction mixture and the mixture was warmed up to 0° C. The reaction mixture was quenched with 270 ml saturated aqueous ammonium chloride containing 30 ml ammonium hydroxide. The reaction mixture was phase separated and the aqueous layer was extracted with ethyl acetate. The organic layers were combined and dried over anhydrous MgSO$_4$. The solid was filtered off and the organic solvent was evaporated off under vacuum. The crude product was purified by chromatography on silica gel using a mixture of hexane and ethyl acetate as a gradient eluent. Yield of the title compound was 18 g (86%).

$^1$H-NMR (CDCl$_3$): δ 7.282 (d, 2H), 6.878 (d, 2H), 5.080~5.211 (m, 1H), 5.029 (s, 2H), 4.057~4.102 (m, 0.5H), 3.716~3.872 (m, 6H), 2.689~2.786 (m, 0.5H), 2.298 (t, 2H), 1.232~2.243 (m, 28H), 0.872~0.951 (m, 12H), 0.548~0.653 (m, 6H)

$^{13}$C-NMR (CDCl$_3$): δ 217.607 (216.675), 173.698, 159.542, 130,061, 128.179, 124.490 (t), 113.894, 104.656 (101.742), 78.538, 75.039 (74.508), 67.107 (66.885), 65,908, 55.243, 54.203 (53.502), 46.659 (46.416), 43.987, 34.286, 32.586 (32.389), 30,848 (t), 29.504, 28.973, 28.571, 28.419 (28.396), 28.305 (28.275), 26.430, 24.890, 23.349, 23.075 (23.045), 22.658, 13.913, 6.855, 4.950

Example 16

Benzyl 7-[(1R,2R,3R)-3-benzyloxy-2-(4,4-difluoro-3-triethylsilyloctyl)]-5-oxo-cyclopenty-1-heptanoate

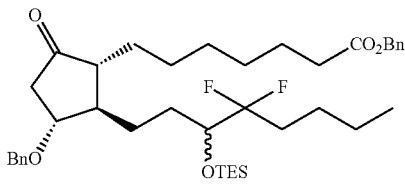

A 1-liter three-necked flask was flame dried and then cooled down under nitrogen. (4,4-difluoro-1-iodooctan-3-yloxy)-triethylsilane of Example 5 (30.5 g, 75 mmol) and 300 ml ether were added to the reaction flask, followed by dropwise addition of tert-butyl-lithium (108 ml, 16% in pentane) at −70° C. A suspension solution of copper cyanide (3.36 g, 38 mmol) in 70 ml ether was cooled to −70° C. and added to the reaction flask while stirring for 30 minutes. Then, a solution of benzyl 7-[5-oxo-3R-(tetrahydrofuranyl-2-yloxy)-cyclopent-1-enyl]heptanoate of Example 10 (10 g, 25 mmol) in 100 ml ether at −70° C. was added to the reaction mixture and the mixture was warmed up to 0° C. The reaction mixture was quenched with 270 ml saturated aqueous ammonium chloride containing 30 ml ammonium hydroxide. The reaction mixture was phase separated and the aqueous layer was extracted with ethyl acetate. The organic layers were combined and dried over anhydrous MgSO$_4$. The solid was filtered off and the organic solvent was evaporated off under vacuum. The crude product was purified by chromatography on silica gel using a mixture of hexane and ethyl acetate as a gradient eluent. Yield of the title compound was 13 g (76%).

$^1$H-NMR (CDCl$_3$): δ 7.235~7.373 (m, 10H), 5.106 (s, 2H), 4.456~4.566 (m, 2H), 3.641~4.007 (m 2H), 1.013~2.683 (m, 29H), 0.883~0.953 (m, 12H), 0.552~0.685 (m, 6H)

$^{13}$C-NMR (CDCl$_3$): δ 217.669 (216.948), 173.615, 137.804 (t), 136.073, 128.551, 128.483, 128.194, 127.845, 127.784, 127.724, 127.602, 79.381 (79.161), 71.654, 70.910, 66.098, 53.809 (53.672), 50.598 (50.507), 46.507 (46.446), 44.382 (44.275), 41.937, 34.522, 30.848 (30.711), 30.036 (29.854), 29.383, 29.072 (29.034), 28.966, 27.854, 26.757, 24.897, 24.214, 23.394, 23.075, 22.658, 13.944, 6.870, 4.912

Example 17

Benzyl 7-[(1R, 2R, 3R)-2-(4.4-difluoro-3-hydroxyoctyl-5-oxo-3-(tetrahydrofuranyl-2-yloxy)-cyclopentyl]heptanoate

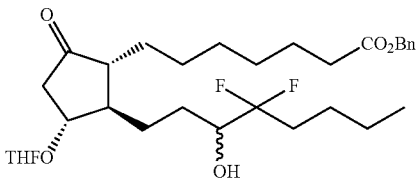

Benzyl 7-[(1R, 2R, 3R)-2-(4,4-difluoro-3-trimethylsilyloctyl)-5-oxo-(tetrahydrofuranyl-2-yloxy) cyclopentyl]-heptanoate of Example 11 (44 g, 70.4 mmol) was dissolved in MeOH (440 ml), followed by addition of formic acid (11 ml) and distilled water (44 ml) and stirred for 3 h at room temperature. The reaction mixture was poured into 500 ml saturated aqueous sodium bicarbonate and stirred for 30 minutes. The reaction mixture was evaporated and the aqueous layer was extracted with 500 ml ethyl acetate. The organic layers were dried over anhydrous magnesium sulfate and the solid was filtered off. The solvent was evaporated off under vacuum. The crude product was purified by chromatography on silica gel using a mixture of hexane and ethyl acetate as a gradient eluent. Yield of the title compound was 30 g (77%).

$^1$H-NMR (CDCl$_3$): δ 7.237~7.316 (m, 5H), 5.038~5.169 (m, 3H), 3.659~4.070 (m, 4H), 0.874~2.725 (m, 34H)

$^{13}$C-NMR (CDCl$_3$): δ 217.236 (216.252), 173.120, 135.695, 128.030, 127.641, 124.053 (t), 103.985 (101.496), 78.420, 75.115 (74.840), 66.695 (66.374), 65.542, 53.550 (52.992), 46.137 (45.595), 45.527 (45.389), 43.527, 33.679, 32.130(32.046), 31.672 (31.534), 28.657, 28.344, 27.931 (27.786) 26.870 (26.588), 26.000, 23.394, 24.328, 23.069 (22.947), 22.176, 13.428

Example 18

4-methoxybenzyl 7-[(1R, 2R, 3R)-2-(4,4-difluoro-3-hydroxyoctyl)-5-oxo-3-(tetrahydrofuranyl-2-yloxy) cyclopentyl]-heptanoate

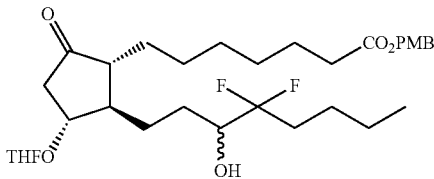

4-Methoxybenzyl 7-[(1R, 2R, 3R)-2-(4,4-difluoro-3-trimethyl-silyloctyl)-5-oxo-3-(tetrahydrofuranyl-2-yloxy) cyclopentyl]heptanoate of Example 12 (169 g, 0.26 mol) was dissolved in MeOH (1.7 L), followed by addition of formic acid (42 ml) and distilled water (170 ml) and stirred for 3 h at room temperature. The reaction mixture was poured into 2 L saturated aqueous sodium bicarbonate and stirred for 30 minutes. The reaction mixture was evaporated and the aqueous layer was extracted with 2 L ethyl acetate. The organic layers were dried over anhydrous magnesium sulfate and the solid was filtered off. The solvent was evaporated off under vacuum. The crude product was purified by chromatography on silica gel using a mixture of hexane and ethyl acetate as a gradient eluent. Yield of the title compound was 138 g (91%).

$^1$H-NMR (CDCl$_3$): δ 7.266 (d, 2H), 6.864 (d, 2H), 5.093~5.225 (m, 1H), 5.017 (s, 2H), 3.601~3.960 (m, 6H), 2.696~2.811 (m, 1H), 1.184~2.307 (m, 31H), 0.910 (t, 3 H.)

$^{13}$C-NMR (CDCl$_3$): δ 217.633 (216.620), 173.830, 159.515, 130.011, 126.820, 124.387 (t), 113.867, 104.504 (102.022), 78.910, 75.494 (75.399), 67.456 (66.921), 65.912, 55.209, 53.866 (t), 46.663 (45.790), 44.055, 34.203, 32.560 (32.469), 32.363 (32.120), 29.991 (29.660), 29.330 (29.262), 29.019, 28.780, 28.742, 28.180 (t), 26.996 (26.822), 24.712 (t), 23.493 (23.399), 22.176, 13.428

Example 19

Benzyl 7-[(1R, 2R, 3R)-3-benzyloxy-2-(4,4-difluoro-3-1hydroxyoctyl)-5-oxo-cyclopentyl]heptanoate

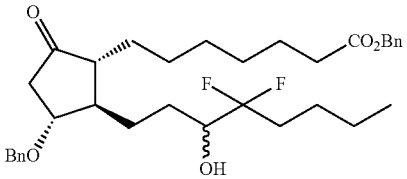 [SMILES: CCCCC(F)(F)C(O)CC[C@H]1[C@H](OCc2ccccc2)CC(=O)[C@@H]1CCCCCCC(=O)OCc1ccccc1]

Benzyl 7-[(1R, 2R, 3R)-2-(4,4-difluoro-3-trimethylsilyloctyl)-5-oxo-3-(tetrahydrofuranyl-2-yloxy) cyclopentyl] heptanoate of Example 13 (13 g, 19 mmol) was dissolved in MeOH (130 ml), followed by addition of formic acid (3.3 ml) and distilled water (13 ml) and stirred for 3 h at room temperature. The reaction mixture was poured into 150 ml saturated aqueous sodium bicarbonate and stirred for 30 minutes. The reaction mixture was phase separated and the aqueous layer was extracted with 150 ml ethyl acetate. The organic layers were dried over anhydrous magnesium sulfate and the solid was filtered off. The solvent was evaporated off under vacuum. The crude product was purified by chromatography on silica gel using a mixture of hexane and ethyl acetate as a gradient eluent. Yield of the title compound was 10 g (86%).

$^1$H-NMR (CDCl$_3$): δ 7.310~7.347 (m, 10H), 5.103 (s, 2H), 4.445~4.591. (m, 2H), 3.669~4.035 (m, 2H), 1.154~2.868 (m, 27H), 0.904~0.937 (t, 3H)

$^{13}$C-NMR (CDCl$_3$): δ 217.918 (216.897), 173.818, 137.966 (137.734), 137.344 (136.034), 128.554, 128.497, 128.190, 128.102, 127.884, 127.586, 124.353 (t), 79.479 (79.418), 72.872 (72.561), 71.680 (70.841), 66.181 (66.147), 65.912, 54.386 (53.908), 50.541, 45.999 (44.420), 43.384 (41.885), 34.226, 31.835 (31.101), 29.308 (29.118), 28.818 (28.484), 27.622 (27.254), 26.556 (26.503), 24.806 (24.723), 24.036 (23.429), 22.742 (22.598), 13.926

Example 20

Benzyl 7-[(1R, 2R, 3R)-2-(4,4-difluoro-3-oxo-octyl)-5-oxo-3-(tetrahydrofuranyl-2-yloxy) cyclopentyl]heptanoate

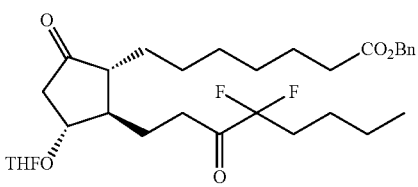

Benzyl 7-[(1R, 2R, 3R)-2-(4,4-difluoro-3-hydroxyoctyl)-5-oxo-3-(tetrahydrofuranyl-2-yloxy)-cyclopentyl]heptanoate of Example 17 (30 g, 54 mmol) in 300 ml toluene was added to 1-liter three-neck flask, followed by addition of TEMPO (1.72 g, 11 mmol), 3% aqueous $NaHCO_3$ (117 ml) and potassium bromide (6.43 g, 54 mmol). The reaction mixture was cooled down to 0° C. and 12% NaOCl (42 ml) was dropwise added to this flask. The brown solution was quenched with aqueous $Na_2S_2O_3$ and extracted with ethyl acetate. The organic layer was dried over anhydrous magnesium sulfate and the solid was filtered off. The solvent was evaporated off under vacuum. The crude product was purified by chromatography on silica gel using a mixture of hexane and ethyl acetate as a gradient eluent. Yield of the title compound was 24 g (80%). $^1$H-NMR ($CDCl_3$): δ 7.183~7.302 (m, 5H), 5.084~5.169 (m, 1H), 5.019 (s, 2H), 4.285~4.309 (m, 1H), 3.709~3.771 (m, 2H), 1.166~3.017 (m, 30H), 0.826 (t, 3H)

$^{13}$C-NMR ($CDCl_3$): δ 216.063, 173.563, 135.979, 128.446, 128.071, 124.549, 102.604 (102.382), 80.084, 67.183 (66.867), 66.001, 59.098 (57.611), 48.748 (48.662), 41.915 (40.421), 34.173, 32.600 (32.471), 31.417 (31.354), 30.476 (t), 29.062 (29.029), 28.931, 28.232, 26.774, 24.759, 24.643, 23.485 (23.242), 22.922, 22.473, 13.823

Example 21

4-Methoxybenzyl 7-[(1R, 2R, 3R)-2-(4,4-difluoro-3-oxo-octyl)-5-oxo-3-(tetrahydrofuranyl-2-yloxy) cyclopentyl]heptanoate

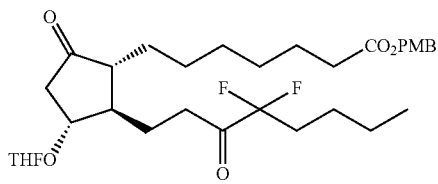

4-Methoxybenzyl 7-[(1R, 2R, 3R)-2-(4,4-difluoro-3-hydroxyoctyl)-5-oxo-3-(tetrahydrofuranyl-2-yloxy)-cyclopentyl]heptanoate of Example 18 (90 g, 154 mol) in 900 ml toluene was added to 2-liter three-neck flask, followed by addition of TEMPO (4.68 g, 30 mmol), 3% aqueous $NaHCO_3$ (324 ml) and potassium bromide (17.4 g, 150 mmol). The reaction mixture was cooled down to 0° C. and 12% NaOCl (162 ml) was dropwise added to this flask. The brown solution was quenched with aqueous $Na_2S_2O_3$ and extracted with ethyl acetate. The organic layer was dried over anhydrous magnesium sulfate and the solid was filtered off. The solvent was evaporated off under vacuum. The crude product was purified by chromatography on silica gel using a mixture of hexane and ethyl acetate as a gradient eluent. Yield of the title compound was 70 g (78%).

$^1$H-NMR ($CDCl_3$): δ 7.277 (d, 2H), 6.873 (d, 2H), 5.084~5.176 (m, 1H), 5.026 (s, 2H), 3.774~4.095 (m, 6H), 2.729~2.916 (m, 3H), 2.299 (t, 2H), 2.145 (ddd, 1H), 1.213~2.030 (m, 24H), 0.892 (t, 3H)

$^{13}$C-NMR ($CDCl_3$): δ 216.772 (215.732), 201.599 (201.075) 176.175, 159.541, 130.038, 128.216, 118.387, 113.893, 104.686 (101.943), 79.293 (75.323), 67.426 (67.024), 65.881, 55.259, 54.063 (53.528), 46.841 (45.410), 45.296 (44.059), 34.272, 34.131 (34.006), 32.579 (32.556), 32.287 (32.013), 29.471 (29.452), 28.901, 27.960 (27.858), 26.442, 25.725, 24.852, 23.459, 23.323 (23.258), 22.408, 13.751

Example 22

Benzyl 7-[(1R, 2R, 3R)-3-benzyloxy-2-(4,4-difluoro-3-oxo-octyl)-5-oxo-cyclopentyl]heptanoate

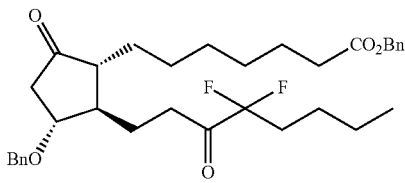 [SMILES: CCCCC(F)(F)C(=O)CC[C@H]1[C@H](OCc2ccccc2)CC(=O)[C@@H]1CCCCCCC(=O)OCc1ccccc1]

Benzyl 7-[(1R, 2R, 3R)-3-benzyloxy)-2-(4,4-difluoro-3-hydroxyoctyl)-5-oxo-cyclopentyl]heptanoate of Example 19 (10 g, 17.5 mmol) in 100 ml toluene was added to 500 ml three-neck flask, followed by addition of TEMPO (0.55 g, 3.5 mmol), 3% aqueous $NaHCO_3$ (38 ml) and potassium bromide (2.1 g, 17.5 mmol). The reaction mixture was cooled down to 0° C. and 12% NaOCl (19 ml) was dropwise added to this flask. The brown solution was quenched with aqueous $Na_2S_2O_3$ and extracted with ethyl acetate. The organic layer was dried over anhydrous magnesium sulfate and the solid was filtered off. The solvent was evaporated off under vacuum. The crude product was purified by chromatography on silica gel using a mixture of hexane and ethyl acetate as a gradient eluent. Yield of the title compound was 9 g (90%), $^1$H-NMR ($CDCl_3$): δ 7.294~7.357 (m, 10H), 5.108 (s, 2H), 4.423~4.556 (m, 2H), 3.782~3.952 (m, 1H), 2.900 (t, 1H), 2.738 (t, 1H), 1.197~2.691 (m, 24H), 0.889~0.938 (m, 3H)

$^{13}$C-NMR ($CDCl_3$): δ 216.973 (215.831), 201.166 (200.661), 173.583, 137.818 (137.617), 136.125, 128.535, 128.171, 127.943, 127.875, 127.605, 118.501 (118.417), 79.658, 71.767 (70.982), 66.056, 54.048, 50.583, 45.475 (44.473), 43.475 (42.021), 34.313 (34.230), 32.279 (32.154), 29.425 (29.300), 28.898, 28.268 (27.376), 26.545 (25.881), 24.863, 24.245, 23.296 (23.216), 22.400 (22.389), 19.858, 13.770

Example 23

Benzyl 7-[(2R, 4aR, 5R, 7aR)-2-(1,1-difluoropentyl)-octahydro-2-hydroxy-6-oxo-cyclopenta[b]pyran-5-yl) heptanoate

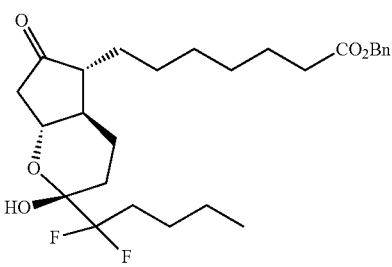 [SMILES: CCCCC(F)(F)[C@@]1(O)CC[C@H]2[C@@H](CC(=O)[C@@H]2CCCCCCC(=O)OCc2ccccc2)O1]

Benzyl 7-[(1R, 2R, 3R)-2-(4,4-difluoro-3-oxo-octyl)-5-oxo-3-(tetrahydrofuranyl-2-yloxy) cyclopentyl) heptanoate of Example 20 (24 g, 44 mmol) in 240 ml acetonitrile was added to 1-liter three-neck flask, followed by addition of distilled water (24 ml) and 3N HCl (2.4 ml) and stirred 1 h at room temperature. The reaction mixture was poured into 100 ml saturated aqueous sodium bicarbonate and stirred for 30 minutes. The reaction mixture was evaporated and the aqueous layer was extracted with 250 ml ethyl acetate. The organic layers were dried over anhydrous magnesium sulfate and the solid was filtered off. The solvent was evaporated off under vacuum. The crude product was purified by chromatography on silica gel using a mixture of hexane and ethyl acetate as a gradient eluent. Yield of the title compound was 20 g (95%).

$^1$H-NMR (CDCl$_3$): δ 7.288~7.366, (m, 5H), 5.100 (s, 2H), 4.133~4.191 (m, 1H), 3.146 (br s, 1H), 2.548 (dd, 1 H), 2.338 (t, 2H), 2.235 (dd, 1H), 1.245~2.030 22H), 0.925 (t, 3H)

$^{13}$C-NMR (CDCl$_3$): δ 213.977, 173.595, 135.977, 128.450, 128.313, 128.175, 128.092, 128.076, 122.267 (t), 97.031 (dd), 71.489, 66.031, 53.076, 45.870, 43.550, 34.153, 30.359 (t), 29.351 (29.305), 28.771, 27.893, 27.107, 26.870, 24.748, 23.458, 22.924 (22.893), 22.489, 13.804

Example 24

4-Methoxybenzyl 7-[(2R, 4aR, 5R, 7aR)-2-(1,1-difluoropentyl)-octahydro-2-hydroxy-6-oxo-cyclopenta[b]pyran-5-yl)heptanoate

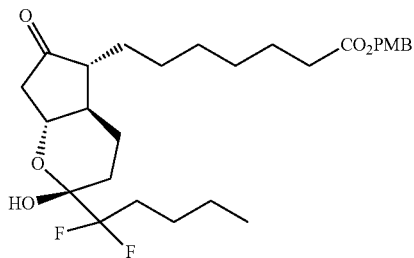

4-Methoxybenzyl 7-[(1R, 2R, 3R)-2-(4,4-difluoro-3-oxo-octyl)-5-oxo-3-(tetrahydrofuranyl-2-yloxy) cyclopentyl) heptanoate of Example 21 (70 g, 120 mmol) in 700 ml acetonitrile was added to 2-liter three-neck flask, followed by addition of distilled water (70 ml) and 3N HCl (7 ml) and stirred for 1 h at room temperature. The reaction mixture was poured into 300 ml saturated aqueous sodium bicarbonate and stirred for 30 minutes. The reaction mixture was evaporated and the aqueous layer was extracted with 1 L ethyl acetate. The organic layers were dried over anhydrous magnesium sulfate and the solid was filtered off. The solvent was evaporated off under vacuum. The crude product was purified by chromatography on silica gel using a mixture of hexane and ethyl acetate as a gradient eluent. Yield of the title compound was 60 g (97%).

$^1$H-NMR (CDCl$_3$): δ 7.285 (d, 2H), 6.883 (d, 2H), 5.040 (s, 2H), 4.109~4.198 (m, 1H), 3.799 (br s, 3H), 3.171 (br s, 1H), 2.551 (dd, 1H), 2.314 (t, 2H), 2.242 (dd, 1H), 1.240~2.039 (m, 22H), 0.934 (t, 3H)

$^{13}$C-NMR (CDCl$_3$): δ 213.924, 173.644, 159.476, 129.928, 128.126, 122.262 (t), 113.833, 97.010 (t), 71.476, 65.828, 53.166, 53.063, 45.884, 43.536, 34.178, 30.339 (t), 29.336, 28.753, 27.881, 27.105, 26.871, 24.739, 23.457, 22.918, 22.479, 13.820

Example 25

7-[(2R, 4aR, 5R, 7aR)-2-(1,1-difluoropentyl)-octahydro-2-hydroxy-6-oxo-cyclopenta [b]pyran-5-yl) heptanoic acid, Lubiprostone

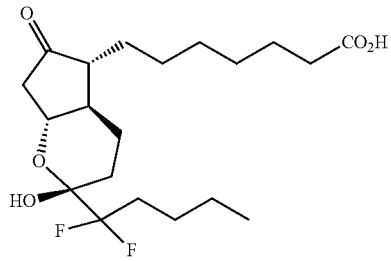 [SMILES: CCCCC(F)(F)[C@@]1(O)CC[C@H]2[C@@H](CC(=O)[C@@H]2CCCCCCC(=O)O)O1]

Method A: 4-Methoxybenzyl 7-[(2R, 4aR, 5R, 7aR)-2-(1,1-difluoro-pentyl)-octahydro-2-hydroxy-6-oxo-cyclopenta[b]pyran-5-yl)heptanoate of Example 24 (60 g, 118 mmol) was dissolved in 600 ml ethyl acetate and followed by addition of 5% palladium on charcoal under hydrogen for 3 h. Then, the reaction mixture was filtered with celite pad. The solvent was evaporated off under vacuum. The crude product was purified by chromatography on silica gel using a mixture of hexane and ethyl acetate as a gradient eluent to obtain 40 g oil product (purity≥99.0%, by HPLC). The oil product was dissolved in isopropyl ether (40 ml) and n-pentane (120 ml) was added while stirring over 12 h. The solid was filtrated off, washed with n-pentane, and dried at 40° C. under vacuum to obtain 31 g white crystalline compound (Yield : 68%, purity≥99.9% by HPLC).

Method B: Benzyl 7-[(1R, 2R, 3R)-3-benzyloxy -2-(4,4-difluoro-3-oxo-oetyl)-5-oxo-cyclopentyl ]heptanoate of Example 22 (2 g, 3.5 mmol) was dissolved in 25 ml ethyl acetate and followed by addition of 5% palladium on charcoal under hydrogen for 1 h. Then, the reaction mixture was filtered with celite pad. The solvent was evaporated off under vacuum. The crude product was purified by chromatography on silica gel using a mixture of hexane and ethyl acetate as a gradient eluent to obtain 1.2 g oil product. The oil product was dissolved in isopropyl ether (3 ml) and n-pentane (10 ml) was added while stirring over 12 h. The solid was filtrated off, washed with n-pentane, and dried at 40° C. under vacuum to obtain 0.95 g white crystallite compound was also obtained (Yield 69%, purity≥99.9% by HPLC).

$^1$H-NMR (CDCl$_3$): δ 4.127~4.199 (m, 1H), 2.553 (dd, 1H), 2.323 (t, 2H), 2.233 (dd, 1H), 1.296~2.000 (m, 24H), 0.914 (t, 3H)

$^{13}$C-NMR (CDCl$_3$): δ 214.081, 179.782, 122,296 (t), 97.158 (t), 71.588, 53.137, 45.926, 43.604, 33.911, 30.488 (t), 29.403, 28.765, 27.968, 27.156, 26.928, 24.530, 23.498, 22.966 (t), 22.557, 13.912

MS (EI): m/e 390 (M$^+$), 372 (M$^+$-H$_2$O), 354 (M$^+$-2 H$_2$O)

Anal. Calcd for C$_{20}$H$_{32}$F$_2$O$_5$:C, 61.52; H, 8.26. Found: C, 61.34; H, 8.28

What is claimed is:

1. A process for preparing Lubiprostone, comprising the steps of:

(1) coupling a cyclopentenone of Formula 1:

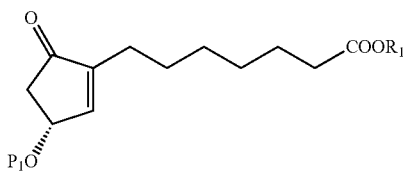

1 wherein R$_1$ is C$_{1-7}$-alkyl, aryl or aralkyl, each of which is unsubstituted or substituted by C$_{1-4}$-alkyl, nitro, halogen or alkoxy; and P$_1$ is a protective group for hydroxyl group, with a cuprate derived from a compound of Formula 2a:

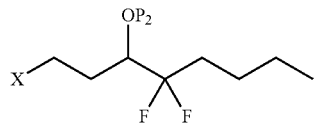

2a wherein P$_2$ is a protective group for hydroxyl group; and X is Cl, Br or I, to form a compound of Formula 3:

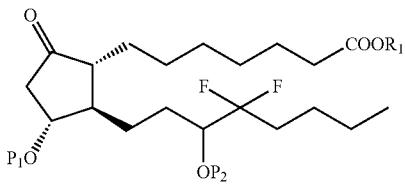

3 wherein R$_1$, P$_1$ and P$_2$ are as defined above;

(2) removing the P$_2$ group and oxidizing the hydroxyl group in ω-side chain to form a compound of Formula 5:

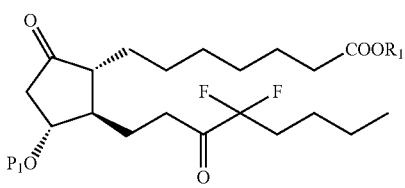

5 wherein R$_1$ and P$_1$ are as defined above; and (3) removing the P$_1$ and R$_1$ groups.

2. A compound of Formula 2:

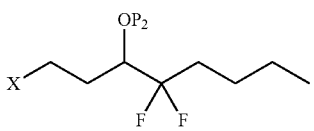

2 wherein P$_2$ is a protecting group for hydroxyl group or H; and X is Cl, Br or I.

* * * * *